United States Patent
Hartmeister

[11] Patent Number: 5,284,487
[45] Date of Patent: Feb. 8, 1994

[54] SURGICAL COMPRESSION FORCEPS

[76] Inventor: Ruben J. Hartmeister, 1034 6th St., Golden, Colo. 80403

[21] Appl. No.: 923,131

[22] Filed: Jul. 31, 1992

[51] Int. Cl.$^5$ .............................................. A61B 17/28
[52] U.S. Cl. ....................................... 606/205; 81/381
[58] Field of Search ............................... 606/208–211; 81/381, 383

[56] References Cited

U.S. PATENT DOCUMENTS

| | | |
|---|---|---|
| 1,151,772 | 8/1915 | Erickson . |
| 1,219,726 | 3/1917 | Grey . |
| 1,448,238 | 3/1923 | Scmitz . |
| 1,497,696 | 6/1924 | Arbogast . |
| 1,541,248 | 6/1925 | Carlson . |
| 1,866,771 | 7/1932 | Johnson . |
| 1,935,009 | 11/1933 | Bluhm . |
| 2,167,599 | 7/1939 | Yanits . |
| 2,198,953 | 4/1940 | Slaughterback . |

FOREIGN PATENT DOCUMENTS 0057355 7/1891 Fed. Rep. of Germany ........ 81/381
0030528 8/1956 Fed. Rep. of Germany ........ 81/381

Primary Examiner—Peter A. Aschenbrenner
Assistant Examiner—Wm. Lewis
Attorney, Agent, or Firm—Kyle W. Rost

[57] ABSTRACT

A compression forceps with four bar linkage is formed of a stationary handle and jaw connected by a shank area; a moveable jaw; a moveable handle having the approximate shape of a bell crank with major and minor arms; and a connecting link member having first and second opposite ends. The four links are joined at pivots, with a first pivot connecting the major and minor arms of the moveable handle to the rear end of the shank area of the stationary handle and jaw. A second pivot connects the free end of the minor arm to a rear end of the moveable jaw. A third pivot connects a first end of the link to the front end of the shank area of the stationary handle and jaw. A fourth pivot connects the second end of the link to a middle area of the moveable jaw. The compound linkage thus formed operates the jaws with an increase of the relative inside angle between the jaws as the jaws close.

8 Claims, 1 Drawing Sheet

SURGICAL COMPRESSION FORCEPS

TECHNICAL FIELD

The invention generally relates to tools and to tool jaws positioned by relatively movable plural handles, such as in pliers. More specifically, the invention relates to pliers with jaw actuating means having pivotal motion about the axis of parallel actuator rods, or with means to articulate or slide both jaws, or with means for arcuate motion of both jaws employing dual pivoted actuator levers, or with means for parallel movement of work-engaging surfaces and longitudinal guide means. A further aspect of the invention relates to a wrench, screwdriver or driver therefor, especially to those having a pivoted inner jaw that is spring-pressed, or especially to those having a pivoted side jaw with a rocking link.

BACKGROUND ART

Pliers and forceps are adapted to numerous special purposes. A simple scissors-action plier such as that shown in U.S. Pat. No. 1,866,771 is formed of two levers with integral jaws, joined at a single pivot, such that the mechanical qualities of the tool are a function of the relative position of the pivot along the lengths of the levers.

Greater leverage can be obtained with a compound linkage in which, typically, one handle and jaw, referred to as the stationary handle and jaw, are integrally joined. The second handle and jaw, referred to as the moveable handle and jaw, are separate pieces. For example, a three link operating linkage is taught in U.S. Pat. No. 1,497,696, where the pair of jaws is connected on a single pivot. The moveable jaw is pivoted at its end to the stationary jaw, while it is pivoted at its shank to an end of the moveable handle. The moveable handle, in turn, is pivoted at its shank to the shank of the stationary handle. This operating linkage has three links, and the pivot at the shanks of the two handles is a sliding pivot point. The mechanical qualities of this tool are a function of both the location of the pivot between the two handles and the location of the pivot between the second handle and moveable jaw.

Another three link system is found in U.S. Pat. No. 1,448,238, in which the moveable jaw is pivoted at its shank to a shank of the stationary jaw. The moveable handle is pivoted at its shank to the shank of the stationary handle. Finally, the end of the stationary jaw is pivoted on a sliding junction to the end of the moveable jaw.

In other variations of plier linkages, the moveable jaw may slide. For example, U.S. Pat. No. 2,167,599 shows a sliding jaw in a tool for coupling railroad cars. Similarly, U.S. Pat. No. 1,935,009 employs a three link system. In this patent, each jaw is integral with its handle, but the shanks of the handles are joined by a pivot link, while the jaws cross at a sliding junction. Still another sliding junction is found in U.S. Pat. No. 2,198,953, wherein the moveable and stationary handles are joined by a toggle link that pushes forward a cam as the handles are closed. In turn, the cam forces the moveable jaw to close along the sliding junction.

Four bar linkages also are used for improved leverage. A four bar linkage in a plier is found in U.S. Pat. No. 1,151,772. A stationary handle and jaw are employed in combination with a moveable handle that is pivoted at its shank to the shank of the stationary handle. The moveable jaw is pivoted at its end, separately to the stationary jaw. Finally, the moveable handle is pivoted at its end to an intermediate link that is also joined to the shank of the moveable jaw. The operating linkage is a parallelogram having equal opposite sides. No sliding pivot point is required, since the parallelogram can change its configuration over a wide range of shapes by pivoting at all four corners.

Another four bar linkage is found in U.S. Pat. No. 1,541,248, in which the moveable handle has the shape of a bell crank. The bend of the crank is pivoted to a rear end of the moveable jaw, while the tip of the crank is pivoted to an end of an intermediate link. This link, in turn, is pivoted at its opposite end to the stationary jaw. The moveable jaw and stationary jaw are joined at their shanks by another pivot.

Still another four bar linkage is found in U.S. Pat. No. 1,219,726, relating to a clamping handle for frying pans. In this patent, the moveable handle again is in the shape of a bell crank. The bend of the crank is pivoted to the stationary handle, while the tip of the crank is pivoted to an end of an intermediate link. The moveable jaw also has a shape similar to a bell crank and is pivoted at its bend to the stationary jaw, while it is pivoted at its rear end to the intermediate link. By this arrangement, closing the handles causes both bell cranks to pivot, closing the jaws.

Many of the pliers of the prior art have good gripping ability and allow application of considerable force. However, they have not been adaptable to certain types of tasks. It would be desirable to have a forceps or plier that not only grips, but also has a grasping motion. In particular, it would be desirable to have a forceps that tends to draw-in the grasped object, as contrasted to merely pinching it. Such a tool should offer action similar to that of the human hand, which draws in a grasped object.

Similarly, a tool employed in surgical procedures should allow careful modulation of applied force. The surgeon must be careful that mechanical tools do not injure a patient due to lack of sensitivity and feel.

To achieve the foregoing and other objects and in accordance with the purpose of the present invention, as embodied and broadly described herein, the forceps of this invention may comprise the following.

DISCLOSURE OF INVENTION

Against the described background, it is therefore a general object of the invention to provide an improved surgical compression forceps that is capable of exerting a grasping action, wherein the angle of the jaws draws in the work piece as the jaws close.

A further object is to provide a forceps in which the jaws are narrow and can enter the very narrow opening of certain surgical incisions or go between the lamina of the backbone or other objects where little room is available.

A further object is to provide a deep throat in a forceps, which enables use of such a tool in back surgery.

A specific object is to provide a forceps that is especially adapted to moving bone hooks, bone screws, and the like along implant rods without slippage.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

According to the invention, a compression forceps having an unequal, four bar linkage, is formed of a stationary handle and jaw connected by a shank area, and a moveable jaw. A moveable handle has the approximate shape of a bell crank having major and minor arms. The forceps further includes a connecting link member having first and second opposite ends. A first pivot connects the approximate intersection of the major and minor arms of the moveable handle to the rear end of the shank area of the stationary handle and jaw. A second pivot connects the free end of the minor arm to a rear end of the moveable jaw. A third pivot connects a first end of the connecting link to the front end of the shank of the stationary handle and jaw. A fourth pivot connects the second end of the link to a middle area of the moveable jaw. The four pivots define between themselves a four bar, unequal length, compound linkage operating the jaws to produce an increase of the inside jaw angle as the jaws close.

The accompanying drawings, which are incorporated in and form a part of the specification illustrate preferred embodiments of the present invention, and together with the description, serve to explain the principles of the invention. In the drawings:

BEST MODE FOR CARRYING OUT THE INVENTION

Figure 1:
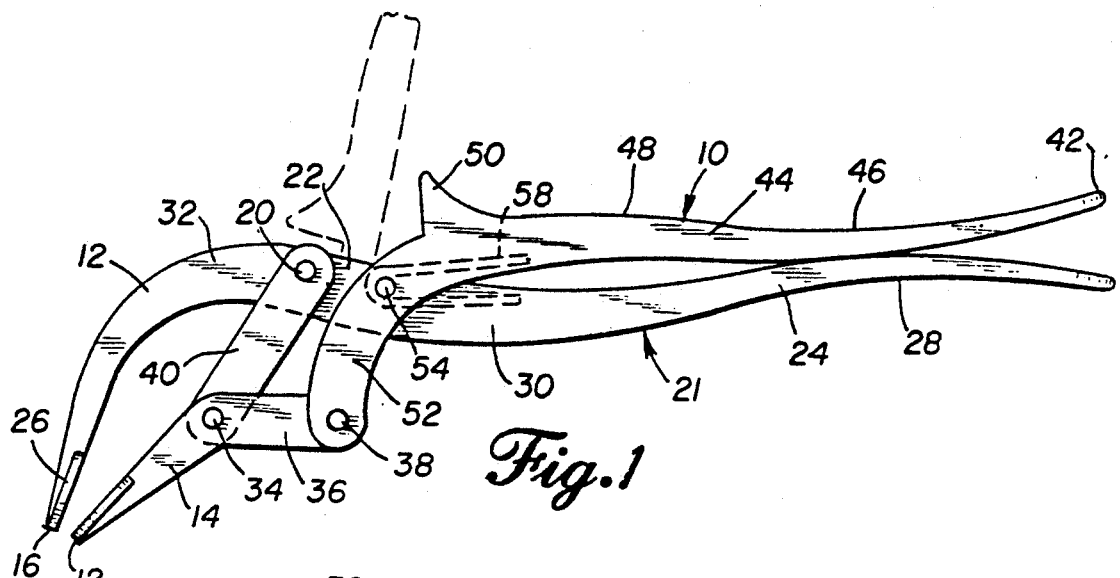
FIG. 1 is a side elevational view of the surgical compression forceps in closed position, and showing in broken lines the handle position of the forceps in open position.
Figure 2:
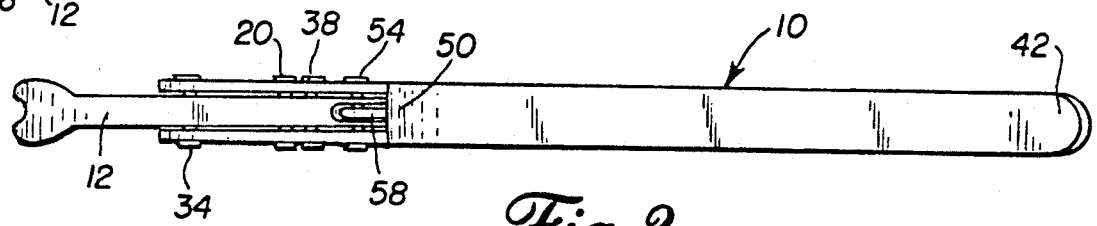
FIG. 2 is a top plan view thereof.

With reference to the drawings, and particularly FIGS. 1 and 2, the surgical compression forceps 10 is a plier-like instrument that is provided with a compound linkage to the jaws in order to achieve a grasping and squeezing motion similar to the closing of the human hand. This instrument is especially designed for use in the surgical arena, where the human hand requires extension in order to reach certain areas and to perform certain tasks that might demand a combination of grasping action, sensitive touch, and extra power. This achievement enables this forceps to be used in surgical procedures, especially in back surgery, where it is desirable that an instrument not slip. Further, the surgeon maintains a sense of feel for the amount of applied force, so that the surgeon is not likely to harm the patient by application of too much pressure to bones or bone screws. A specific task for which the instrument is designed is rearranging of vertebra lamina in connection with back surgery. Particularly, the instrument is adapted for use along an implant rod, to position various hooks and screws that are to be fastened to the rod. This positioning process often is part of the process of straightening a curved backbone and can require both considerable force and precision. For this purpose, the jaw tips are configured to engage an implant rod and work along the longitudinal axis of the rod. The grasping motion of the jaws is well suited to positioning devices along the rod.

The forceps 10 is composed of a stationary handle and jaw and a moveable handle and jaw. As previously explained, the stationary handle and jaw are a one-piece body unit, while the moveable handle and jaw are separate pieces. In FIG. 1, the stationary jaw 12 is the upper jaw, while the moveable jaw 14 is the lower jaw. At their respective forward ends, the upper and lower jaw each has a broad tip 16, 18, while at their rearward ends the jaws are joined by pivot connections to opposite ends of an intermediate link member 40. Together, the jaws define a deep throat. A resilient means biases the jaws to open position, so that the forceps can be operated with one hand.

The stationary jaw 12 is formed as one portion of a larger, stationary body member 21 that includes a intermediate shank portion 22 and a first, lower, stationary handle grip 24. The jaw itself has a broad, flat, working surface 26 on jaw tip 16, and this working surface is shown in greater detail in FIG. 3.

FIG. 1 shows the general configuration of the stationary body member 21, in which the handle 24 and shank 22 are generally longitudinally aligned. However, the handle grip 24 has a slight upward curve 28, such as on a nine inch radius, to serve as a comfortable reception area for the hand. Likewise, near the center of body 21 may be a slight downward curve 30, for example also on a nine inch radius. Despite these two curves and other minor variations, the handle and shank generally follow a longitudinal axis from the rear tip of the handle grip to point 20 at the forward end of the shank, at the unitary junction of the shank with the rear end of the stationary jaw. The major deviation from such an axis is found in the jaw, which curves downwardly by slightly less than a right angle, according to the view of FIG. 1. The mid-portion 32 of the jaw is bent on a tight curve, such as a one and one-half inch radius, until the working face 26 of the jaw is located at a preferred angle of about sixty-eight degrees to the axis of the handle and shank. In overall preferred dimensions, the stationary body member 21 is about ten and one-half inches in length and three inches in height.

Figure 3:
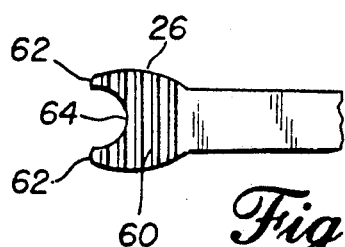
FIG. 3 is an enlarged view of the tip of one jaw of the forceps.

The moveable jaw 14 of the forceps is provided with a broad, flat, working surface 26 at its tip 18 that is substantially identical to that on the stationary jaw, as shown in FIG. 3. The jaw is composed of two arms formed with a unitary connection, wherein the arm containing the working surface 26 extends rearward from the tip 18 for slightly less than two-thirds the height of the body 21, to a bend at a point 34 located in a central area of the jaw's length. For example, the forward portion of jaw 14 may be slightly less than two inches in length, from tip 18 to point 34. The moveable jaw member then changes angle by about thirty-five to forty-five degrees and the jaw continues rearward as a rear jaw arm portion 36, having a typical length of about one and one-half inches. The moveable jaw has pivot points joining it to other portions of the forceps, located near the opposite ends of rear arm 36, with the spacing between the pivot points being about one and one-quarter inch. The forward pivot point 34 is located approximately at the bend defining the interface of the forward jaw arm and rear jaw arm portions, while the rear pivot point 38 is located slightly before the rear end of the rear jaw arm. In general, the moveable jaw resembles a bell crank wherein the rear arm is bent downwardly by about forty-five degrees from the front arm. Therefore, as measured from the bottom of the moveable jaw according to the position shown in FIG. 1, the angle at the junction of its two arms is an obtuse angle in the range of about one hundred thirty-five to one-hundred forty-five degrees.

The body 21 and the moveable jaw 14 are joined to each other by the connecting link member 40. One end of the link is connected to pivot point 34 by any suitable connecting means, such as a screw, rivet, or the like, generally referred to as being a pivot pin. The second end of link 40 is connected to the shank 22 of body 21 at a pivot point 20 by a second connecting means or pivot pin. Pivot point 20 is at the forward end of shank 22, about 2.6 inches rearward of the tip of the body. The length of link 40 between pivot points 20 and 34 is about one and three-quarters inch.

The second, moveable handle lever 42, is connected to both the body 21 and the lower jaw 14. This handle lever 42 is generally in the shape of another bell crank. The major arm of the crank is a grip portion 44 that is substantially a mirror image of the lower handle grip 24, having a downward curve 46 approximately corresponding to curve 28 and having an upward curve 48 approximately corresponding to curve 30. An upstanding guard member 50 is located at the forward end of the grip portion. Thereafter, lever 42 defines the second, minor arm of the bell crank as a front end portion 52, curving downwardly by about ninety degrees. The free end of the minor arm 52 is joined to the rear portion 36 of the moveable jaw arm at pivot point 38. A pivot point 54 at the approximate intersection of the major and minor bell crank arms is joined to the rear end of shank 22. The shank is defined as extending between pivot points 20 and 54. Also, the stationary handle and moveable handle cross each other in the proximity of pivot point 54.

The orientation of the four bar linkage and pivot points at the corners of the linkage of this forceps account for its operation. The spacing between pivot points 38 and 54 may be approximately one and three-eights inches. As noted above, the spacing between pivot points 34 and 38 may be approximately one and one-quarter inch, while the spacing between points 20 and 34 is about one and three-quarters inch. In addition, pivot point 54 is located about three-fourths of an inch rearward of pivot point 20 in the orientation of FIG. 1. The system of the four pivot points 20, 34, 38, and 54, together with the four bar linkage defined by link 40, rear jaw arm 36, minor arm 52, and shank 22, define the compound linkage that enables the forceps to operate in a unique manner. The four bars of this linkage define a quadrangle, in this case a rhomboid, in which all sides are unequal and opposite sides are not parallel. The rear jaw arm 36 is opposite the shank 22, while the link 40 is opposite the minor bell crank arm 52. If the minor arm 52 is taken as a base dimension, the shank 22 is about 50% to 60% of this length; the connecting link 40 is about 120% to 130% of the base length; and the jaw arm is about 85% to 95% of the length.

These approximate proportions have been found to produce the best action and preferred operation of the instrument. As the instrument is closed, the second bell crank formed by the moveable handle sweeps forward the first bell crank defined by the moveable jaw. Pivot point 34 is on a longer arm than pivot point 38, with the result that the moveable jaw closes on the stationary jaw with a slight closing of the angle between the jaws. According to the preferred embodiment, the jaws do not come into contact when the instrument is fully closed. A space of about one-quarter to three-eighths inch remains between the tips of the jaws when the two handles are brought together. The handle grips are biased into open position by a spring 58 located about a pivot pin at point 54, so that the forceps can be closed when operated by a single hand.

The working faces on jaw tips 16 and 18 are shown in FIG. 3, both faces being substantially identical. Faces 26 have a serrated surface 60 in order to provide high friction with any grasped object. Further, the tip of the jaws have separated prongs 62, defining an inward curved recess 64, which is capable of straddling an implant rod. Thus, the forceps is especially suited for moving bone screws or clamps along an implant rod without slipping.

Figure 4:
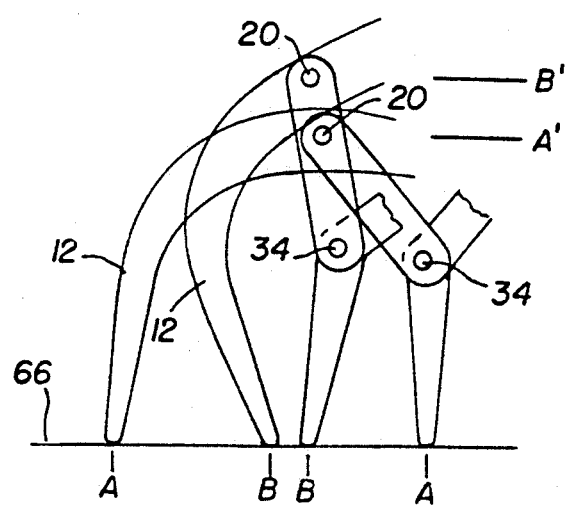
FIG. 4 is a compound side elevational view of the forceps jaw portion in both open and closed positions, showing the change in jaw depth as the jaw tips move with respect to a fixed base line.

The operation of the forceps is best shown in FIG. 4. The compound linkage described above causes the jaws to move between open and closed positions with a substantial deepening of the throat. For example, the jaws are moved with their tips following a base line 66, which approximates the action of the jaws when following the surface of an implant rod. The throat depth can be measured between the base line and pivot point 20. Jaws 12 and 14 in open position are designated at points A on the base line, which may be about three inches apart. In closed position they are designated by points B on the baseline, which may be about one-quarter inch apart. Point 20 in open position is designated at A', while in closed position it is at B'. The distance from A' to B' is the deepening of the throat as the jaws close over a span of slightly less then three inches. This deepening may be about one-quarter inch for the dimensions given in the preferred embodiment.

Upon closing the instrument, this deepening of the throat is accompanied by a very slight closing in the angle of the moveable jaw relative to the stationary jaw, as described above. When fully open, the jaws may have a slight outwardly open angle, for example fifteen degrees. As they close, the jaws become parallel at about two inches of separation. Upon further closing, the jaws assume a slight inward or closed angle, for example in the range from five to ten degrees. This small increase in the inside angle is useful in preventing loss of the work piece. Particularly, as the jaws move together along an implant rod or similar base line, such very slight closing of jaw angle better enables the jaws to move a clamp or other work piece along the rod or base line. Any tendency of the forceps to pull away from the base line is reduced, while the forceps pull a work piece along the base line with accuracy. Thus, the possibility for the instrument to slip off the work piece is greatly reduced. The action of the forceps is similar to the grasping action of a human hand in that forces can be directed into a squeezing motion coupled with a retention of grip on the work piece. Because the motion of the jaw accomplishes such grasping motion, the surgeon is better able to concentrate of other aspects of use, such as better controlling force.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

I claim:

1. A compression forceps of the type having a stationary handle and jaw connected by a shank area; a moveable jaw; a moveable handle having the approximate shape of a bell crank with major and minor arms; and a connecting link member having first and second opposite ends; together defining an improved four bar linkage having a first pivot connecting the approximate intersection of the major and minor arms of the moveable handle to the rear end of said shank area of the stationary handle and jaw; a second pivot connecting the free end of said minor arm to a rear end of said moveable jaw; a third pivot connecting a first end of said link to the front end of the shank area of the stationary handle and jaw; and a fourth pivot connecting the second end of the link to a middle area of the moveable jaw; wherein the improvement comprises:

an unequal linear spacing between first and second pivots, the first and third pivots, the third and forth pivots, and the second and forth pivots such that the four pivots define therebetween four mutually unequal linkage bars forming a compound linkage capable of operating the jaws with an increase of the relative inside angle between the jaws as the jaws close.

2. The compression forceps of claim 1, wherein each of said jaws comprise:

a serrated working face; and a pair of prongs spaced at opposite lateral sides of the working face and defining there between a recess.

3. The compression forceps of claim 2, wherein said serrated working faces of the jaws have a relative angle therebetween ranging from approximately a ten degree open angle when said faces are at maximum separation, to closed angle of approximately a five to ten degrees when the jaw faces are at minimum separation.

4. The compression forceps of claim 1, wherein said moveable jaw is comprised of a forward jaw portion and a rearward jaw arm, and said forth pivot is connected approximately at the junction thereof; and the face of the moveable jaw is at an acute angle to a line through said second and fourth pivots.

5. The compression forceps of claim 4, wherein said acute angle is in the range approximately from thirty-five to forty-five degrees.

6. The compression forceps of claim 1, wherein said stationary handle and moveable handle intersect each other approximately at said first pivot.

7. The compression forceps of claim 1, wherein:

said four bar linkage is in the shape of a rhomboid; and relative to the distance between the first and second pivots, the distance between said first and third pivots is in the range from about 50% to 60% thereof; the distance between said third and fourth pivots is in the range from about 120% to 130% thereof; and the distance between said second and fourth pivots is in the range from about 85% to 95% thereof.

8. A compression forceps having a four bar linkage, comprising:

a stationary handle and jaw connected by a shank area;

a moveable jaw;

a moveable handle having the approximate shape of a bell crank with major and minor arms; and a connecting link member having first and second opposite ends;

a first pivot connecting the approximate intersection of the major and minor arms of the moveable handle to the rear end of said shank area of the stationary handle and jaw;

a second pivot connecting the free end of said minor arm to a rear end of said moveable jaw;

a third pivot connecting a first end of said link to the front end of the shank area of the stationary handle and jaw;

a fourth pivot connecting the second end of the link to a middle area of the moveable jaw;

wherein said four pivots define therebetween a four bar, unequal length compound linkage capable of operating the jaws with an increase of the relative inside angle between the jaws as the jaws close; and means for resiliently biasing said handles in the direction to open the jaws.

* * * * *